United States Patent [19]

Sarstedt

[11] Patent Number: 5,174,301
[45] Date of Patent: Dec. 29, 1992

[54] BLOOD EXTRACTION DEVICE TESTING METHOD

[75] Inventor: Walter Sarstedt, Nuembrecht-Rommelsdorf, Fed. Rep. of Germany

[73] Assignee: Walter Sarstedt Geraete und Verbrauchsmaterial fuer Medizin & Wissenschaft, Nuembrecht-Rommelsdorf, Fed. Rep. of Germany

[21] Appl. No.: 828,392

[22] Filed: Jan. 30, 1992

Related U.S. Application Data

[62] Division of Ser. No. 587,697, Sep. 25, 1990, Pat. No. 5,095,914.

[30] Foreign Application Priority Data

Sep. 26, 1989 [DE] Fed. Rep. of Germany ....... 3932109

[51] Int. Cl.⁵ .............................................. A61B 5/00
[52] U.S. Cl. ................................... 128/765; 604/220
[58] Field of Search ................... 128/760, 763, 765; 604/110, 220, 209

[56] References Cited

U.S. PATENT DOCUMENTS

| | | | |
|---|---|---|---|
| 201,443 | 3/1878 | Parker | 604/209 |
| 2,369,304 | 2/1945 | Lewis | 604/209 |
| 4,246,898 | 1/1981 | Travalent et al. | 604/220 |
| 4,333,457 | 6/1982 | Marquiles | 604/110 |
| 4,370,987 | 2/1983 | Bazell et al. | 128/760 |
| 4,459,997 | 7/1984 | Sarstedt | 604/110 |
| 4,642,102 | 2/1987 | Ohmori | 604/210 |
| 4,832,696 | 5/1989 | Luther et al. | 604/164 |
| 4,840,616 | 6/1989 | Banks | 604/110 |
| 4,906,231 | 3/1990 | Young | 604/110 |
| 4,978,339 | 12/1990 | Labouze et al. | 604/110 |

FOREIGN PATENT DOCUMENTS

| | | | |
|---|---|---|---|
| 0012528 | 7/1903 | Fed. Rep. of Germany | 604/209 |
| 0669910 | 4/1987 | Switzerland | 604/110 |
| 8900432 | 1/1989 | World Int. Prop. O. | 604/110 |

*Primary Examiner*—Max Hindenburg
*Attorney, Agent, or Firm*—Townsend and Townsend

[57] ABSTRACT

A blood extraction device features an extraction cylinder (11) having a forward end for attaching a needle (12) and a rear end having an opening (13) for a piston rod (14) together with a piston (15) secured to the forward end of the piston rod (14) arranged to slide axially in the extraction cylinder (11). The piston (15) can essentially be moved only in the direction away from the foward end of the extraction cylinder (11) and practically incapable of being moved when subjected to a force in the direction of the forward end due to one-way coacting means of prevention (17, 18).

8 Claims, 4 Drawing Sheets

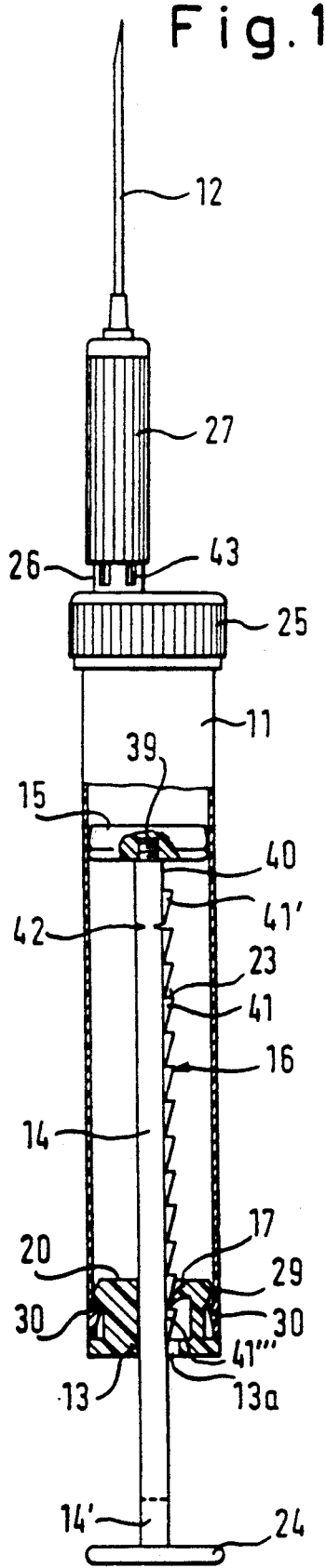
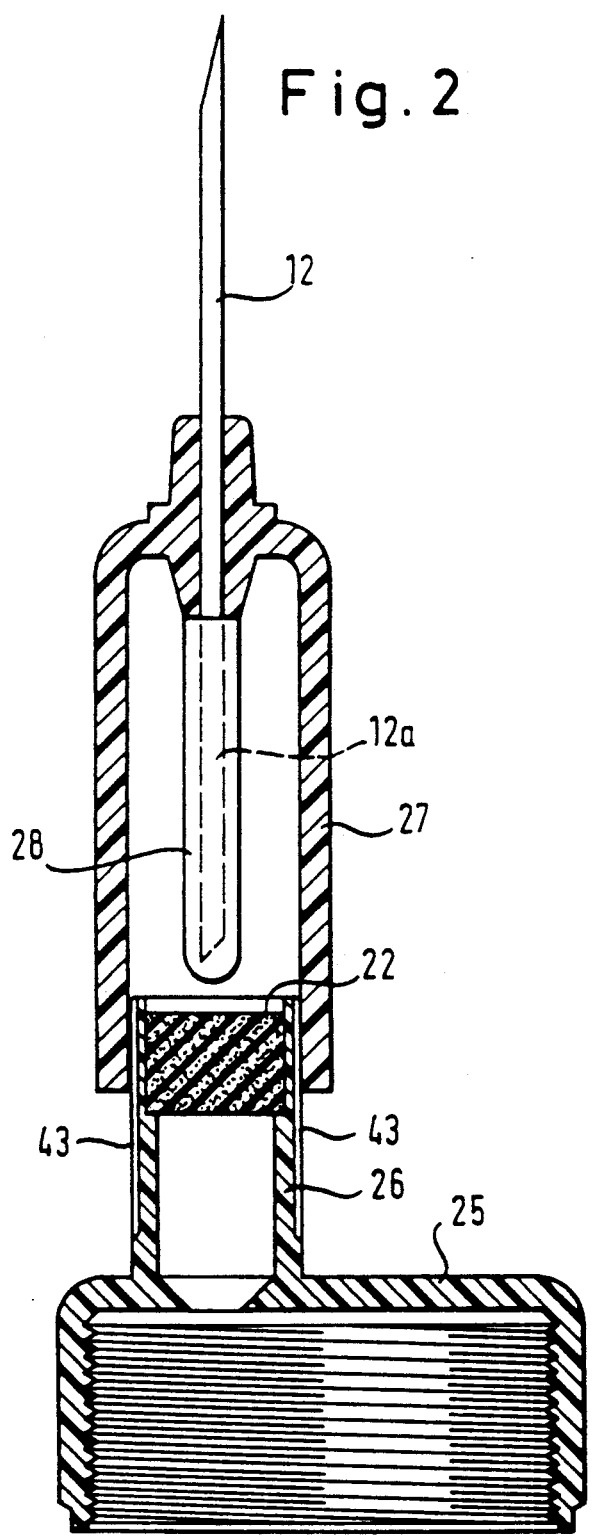

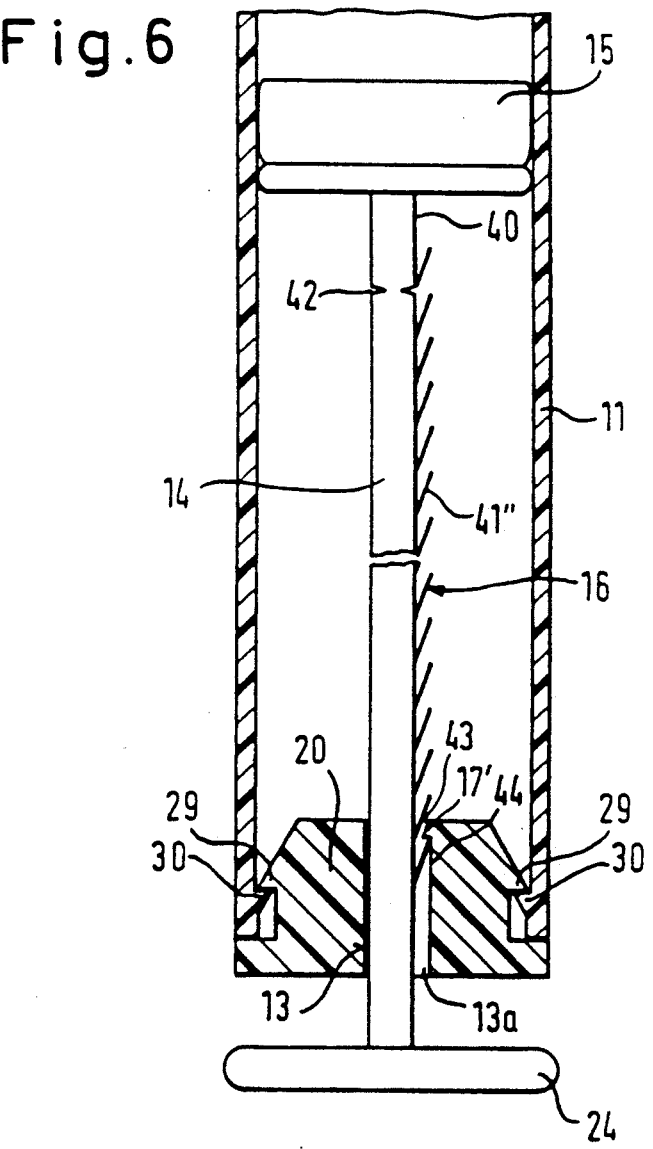

BLOOD EXTRACTION DEVICE TESTING METHOD

This is a divisional application of co-pending U.S. patent application Ser. No. 07/587,697, filed Sep. 25, 1990, for Blood Extraction Device which has since become U.S. Pat. No. 5,085,914.

The invention relates to a method for vacuum testing a blood extraction device.

BACKGROUND OF THE INVENTION

Blood extraction devices (see e.g. DE-PS 29 48 653, 30 49 503) are intended merely to extract blood from, but not to inject any kind of fluid substance into the vein of the patient, although they are generally suitable for this purpose.

In conjunction with disposable syringes it is prior art (DE-Gbm 88 04 656) to prevent repeated use by ratchet means allowing only one charging of the syringe and one injection but not a repeat charging with fluid. For this purpose, however, the barrel of the syringe must be provided with a ratchet ring in the form of a piston sliding with friction within the syringe barrel.

In a further disposable syringe of prior art (U.S. Pat. No. 4,826,483) the piston rod is provided with a plurality of ratchet keys which interact with spring-loaded ratchet shoulders at the bottom of the syringe. By turning the piston rod thru 90° the syringe can be charged and then the fluid injected into, for example, the vein of the patient. Since further turning of the piston rod is prevented by the ratchet key locking into place in a radial notch of the piston rod, this syringe too can only be used once for charging with liquid and injecting this liquid.

Also known as prior art is a blood extraction device (U.S. Pat. No. 4,370,987) the piston rod of which is toothed and the rear end of which has an opening for passage of the piston rod and a stop arranged therein. This is intended to establish the position of the piston in various charging positions to enable a vacuum of prescribed strength to be created in the cylinder. As soon as the vacuum is created in the cylinder the rear sharpened end of a needle inserted in the vein of the patient can be used to puncture a flexible plug located in the forward end of the cylinder thus allowing the vacuum to become active within the needle and draw the blood from the vein of the patient.

However, in this blood extraction device of prior art the opening for passage of the piston rod in the rear end of the cylinder must be so large that the toothing on the piston rod and the stop could possibly disengage thus making it possible to push the piston also forwards which is also intended to eject the received blood into some other receiving vessel. This device of prior art could thus also be misused as a syringe.

This invention is thus based on the device according to U.S. Pat. No. 4,826,483 which is also suitable for blood extraction in which the piston rod is guided in the axial direction relative to the extraction cylinder so that the one-way coacting means cannot be disengaged by radial movements of the piston rod, but only by turning of the piston rod.

SUMMARY OF THE INVENTION

On the basis of a device of this kind the object of the invention is to create a method for vacuum testing a blood extraction device of the aforementioned kind, the use of which as a syringe is rendered impossible, to safely preclude any intentional misuse of the blood extraction device as a syringe.

This is achieved in accordance with the present invention, as is more fully discussed below, by providing an extraction cylinder with a piston reciprocally movably disposed therein and attached to a piston rod protruding from a rear end of the cylinder. The forward end of the cylinder carries a needle and can be sealed. An axial guide plug is provided for the piston rod which can be pushed into the rear opening of the extraction cylinder to thereby close the interior of the cylinder. The piston rod and the plug form a one-way lock which permits movements of the rod and piston relative to the plug in a rearward direction only while preventing such movements in a forward direction toward the needle mounted on the cylinder.

This syringe is vacuum tested in accordance with the present invention by attaching the plug to the rearwardmost end of the rod (the relative position of the rod which corresponds to the positioning of the piston adjacent the forward end of the cylinder when the plug is secured to the rear end of the cylinder) and positioning the plug at the rear end of the cylinder without, however, fastening it thereto. Also, the forward end of the cylinder is sealed, the piston with the plug is pulled slightly rearwardly. This creates a vacuum in the forward portion of the cylinder so that, upon release of the piston, the vacuum causes the return of the piston to its original position (adjacent the front end of the cylinder). Such movement of the piston indicates that there is no leak and the guide plug for the piston can then be snapped into and locked to the rear end of the cylinder.

Of particular advantage is to provide the invention as a blood extraction device with the forward end of the extraction cylinder closed off by a pierceable diaphragm, the latter being preferably provided in a boss of a screw cap screwed on to the forward end of the extraction cylinder (DE-C2-29 48 653). This boss is used to mount a guide sleeve holding a needle sharpened at both ends, the rear end of the needle piercing the diaphragm.

Whereas the forward end of the extraction cylinder should be vacuum tight when retracting the piston for vacuum testing, there should be an air vent at the forward end, e.g., by providing a threaded closure cap which can be unscrewed for pushing the piston into its forward end position after vacuum testing.

This procedure can be combined when inserting the plug in the blood extraction device according to the invention, by the plug still not being inserted in the rear end of the extraction cylinder during vacuum-testing by retracting the piston but preferably already being arranged over the rear end of the piston rod an by the plug being forced into the fitted position when subsequently venting, a projection on the piston rod or the rearmost tooth of the ratchet toothing or the handle at the end of the piston rod transmits the pushing force to the plug, in particular. Thus pushing the plug into the rear end of the extraction cylinder is done in the same procedure as for venting the internal space of this cylinder.

BRIEF DESCRIPTION OF THE DRAWINGS

The invention will now be described in the following for example with reference to the drawing in which:

FIG. 1 is a partly sectioned side view of a blood extraction device in accordance with the invention FIG. 2 is a partly sectioned, enlargened side view of the screw cap located on the forward end of the extraction cylinder according to FIG. 1 showing the components provided

FIG. 5 is a partly sectioned side view analogous to FIG. 3 showing the one-way coacting means in the form of locking means and FIG. 6 is a view similar to FIG. 3 showing a similar arrangement of the one-way coacting means.

DESCRIPTION OF THE PREFERRED EMBODIMENTS

Figure 3:
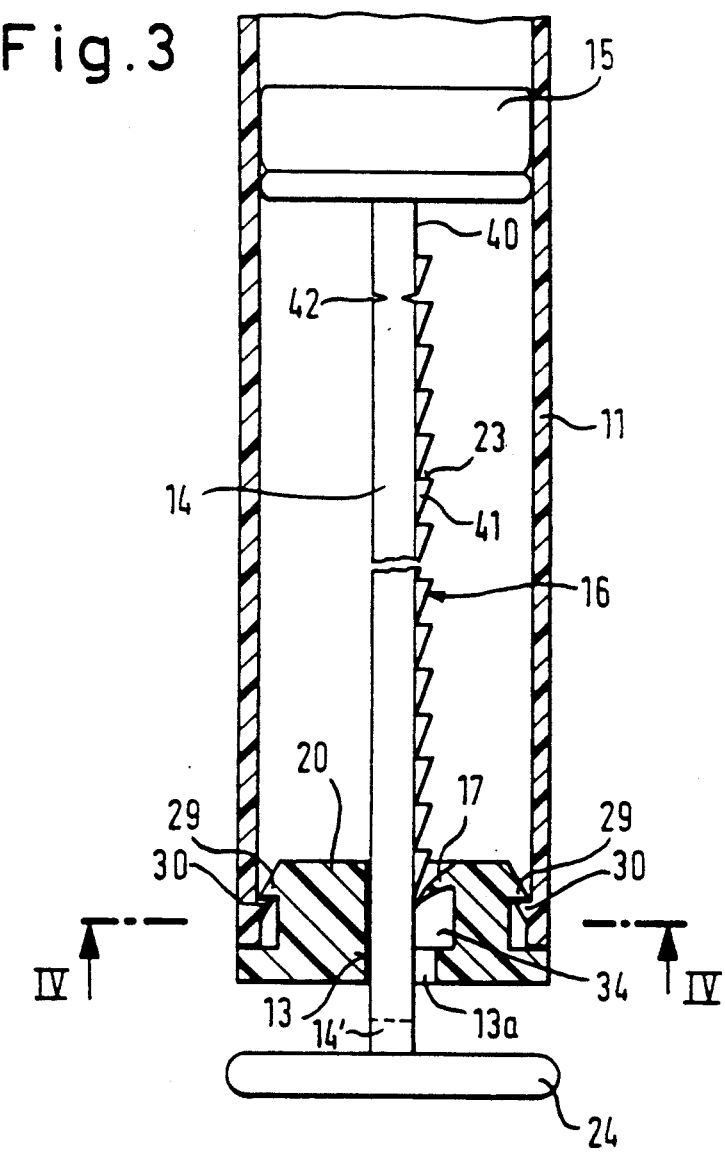
FIG. 3 is a slightly enlargened, partly sectioned side view of the region of the blood extraction device incorporating the one-way coacting means (with reference to FIG. 1)

FIG. 1 shows a rotationally cylindrical extraction cylinder 11 with a screw cap 25 for screwing on to the male thread at its forward end from which a boss 26 extends forwards as shown in FIGS. 1 and 2 in which a piercable diaphragm 22 is arranged. On the rotationally cylindrical hollow boss 26 a guide sleeve 27 having a rotationally cylindrical interior can be mounted, said sleeve holding at its forward end a needle 12 sharpened at both ends, the rear part 12a of which is covered by a flexible tubing 28. In the outer surrounding surface of the boss 26 axial vent grooves 43 are provided.

When mounting the guide sleeve 27 as shown from the position in FIG. 2 the rear end of the needle part 12a pierces the tubing 28 and then the diaphragm 22 thus producing a connection from the forward end of the needle 12 to the interior of the boss 26 and thus to that of the extraction cylinder 11. As soon as the guide sleeve 27 is removed from the boss 26 and part 12a of the needle 12 removed from the diaphragm 22 the tubing 28 automatically envelopes the rear part 12a of the needle 12, whilst the penetration in the diaphragm 22 automatically closes due to the elasticity of the diaphragm.

In the extraction cylinder 11 a piston 15 is arranged as shown in FIGS. 1 and 3 to slide axially tight, into which a piston rod 14 is screwed from the rear at 39 and carrying on the one side as shown in FIGS. 1 and 3 a ratchet toothing 16 extending parallel to the centerline of the piston rod 14, the teeth of which (41) feature a ratchet surface 23 at their end extending essentially vertical to the piston rod 14 whilst slanting to the rear of the piston rod 14.

As shown by FIGS. 1 and 3 an annular plug 20 is inserted in the rear end of the extraction cylinder 11, this plug featuring an axial guide opening 13 for the piston rod 14 and also provided with a spring-loaded ratchet key 17 opposing the ratchet toothing 16. The teeth of the ratchet toothing 16 and of the ratchet key 17 are inclined so that when the piston rod 14 is retracted from the extraction cylinder 11 the ratchet key 17 can detent in one tooth to the next, whilst any attempt to move the piston rod 14 in the direction of the screw cap 25 forces the ratchet key 17 against the ratchet surface 23 of the tooth 41 in place at that time of the ratching toothing 16 thus blocking movement of the piston rod 14 in this direction. The piston rod 14 is held in the guide opening 13 so that it cannot escape from the ratchet key 17. For this purpose the guide opening 13 is formed as shown in FIGS. 1 and 3 so that smooth side of the piston rod 14 facing away from the ratchet toothing 16 is in contact with the wall of the guide opening 13. Diametrally opposed is the passage at 13a somewhat larger to create sufficient room to allow the ratchet toothing 16 to pass and connecting the ratchet key 17 axially to the rear.

It is particularly important that the ratchet key 17 is released, i.e. not located at the level of the ratchet toothing in the basic position as shown in FIG. 3. In this way the ratchet key 17 will not lose its spring force even when the blood extraction device is shelved for a lengthy period.

The plug 20 features locking projections 29 extending radially outward so as to mate with the rear of the companion ratchet projections 30 on the rear end of the extraction cylinder. The ratchet projections 29 and those of the companion ratchet 30 have precisely the reverse ratchet effect to that of the ratchet toothing 16 and the ratchet key 17, i.e. to allow the plug 20 to be inserted from the rear into the extraction cylinder 11 in the direction of the screw cap 25 where it locks into place, whilst axial retraction of the plug 20 to the rear is prevented by the ratchet projections 29 acting together with the companion ratchet 30.

At certain positions around the companion ratchet 30 radial notches 31 (FIG. 4) can be provided to mate the radial projections 32 of the plug 20 to prevent the plug 20 from turning in the extraction cylinder 11.

Figure 4:
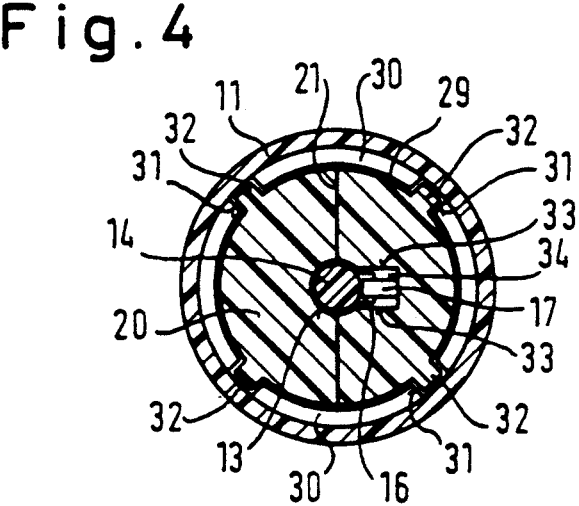
FIG. 4 is a section along line IV—IV in FIG. 3

Rotation control means of this kind are necessary—as shown in FIGS. 1, 3 and 4—to the extent that the ratchet toothing 16 and the ratchet key 17 are provided on one side of the piston rod 14 only. Any other means of rotational control can be used for the plug 20 to ensure that the ratchet toothing 16 and the ratchet key 17 always remain true.

So that the piston rod 14 assumes the correct rotary position with respect to the plug 20, the side flanks 33 (FIG. 4) of a radial recess 34 in the plug 20 in which the ratchet key 17 is accommodated can act together with the ratchet toothing 16 to produce a suitable rotational control. In accordance with the invention, therefore, the plug 20 is located in relation to the extraction cylinder 11 and the piston rod 14 relative to the plug 20 in the prescribed rotational position.

Figure 5:
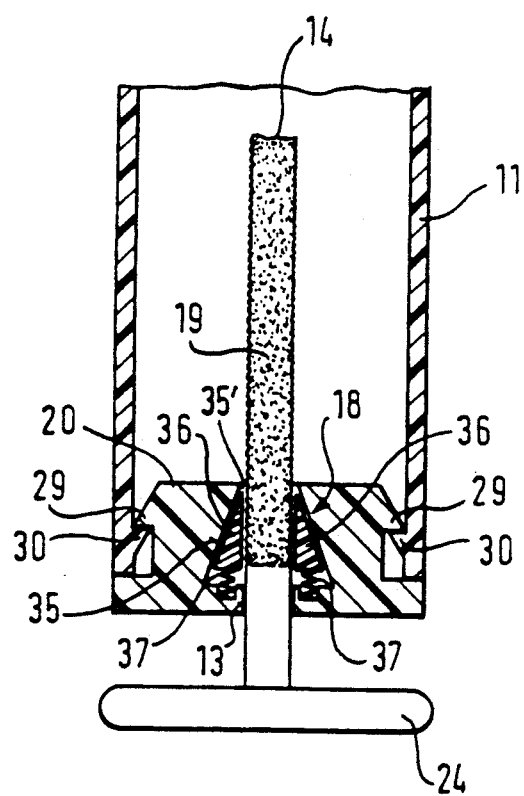

In the embodiment as shown in FIG. 5 diametrally opposed surfaces of the piston rod 14 are provided with a roughened surface 19. In the inside of the port 20 locking means constituting complementary wedges 36 in forward tapering wedge-shaped recesses 35' are provided. These wedges 36 are in friction contact by their radial inside surfaces with the surface 19 of the piston rod 14 by being forced forward due to the springs 37. When the piston rod 14 is removed from the screw cap 25 the wedges 36 lose contact with the wedging 35 tapered in the direction of the screw cap 25 thus allowing the piston rod 14 to be withdrawn.

Should, however, the piston rod 14 be pushed in the direction of the screw cap 25 the wedges 36 will detent between the wedging 35 of the plug 20 and the surfaces 19 of the piston rod 14. This detent supports the action of the springs 37 forcing the wedges 36 from the rear against the wedging 35 tapered forwards. Wedges 36 are also tapered forwards and feature not only locking surfaces adapted to the surface of the piston rod 14 on the inside, but also wedging adapted to the conical surfaces 35 on the outside. Wedges 36 could also be provided all around the piston rod 14 when the latter is roughened all around.

The functioning of the described blood extraction devices is as follows:

When assembled in manufacture the annular plug 20—when in one piece and formed as shown in FIGS. 1 and 3—is first mounted on the rear end of the piston rod 14 in a way as described further below.

The plug 20 is then snapped into place already over the rearmost tooth 41''' before detenting in the rear end of the extraction cylinder 11 as shown in FIG. 1 or it remains on the piston rod piece between the rear end of the ratchet toothing 16 and the handle 24 provided at the end of the piston rod 14.

The piston together with the piston rod 14 and the mounted plug 20 is then inserted into the rear end of the extraction cylinder 11, but only as far so that the plug 20 still protrudes from the rear end of the extraction cylinder 11, i.e. without detenting into place within.

Then the screw cap 25 is screwed into place and vacuum-testing done by withdrawing the piston rod 14, releasing the piston after a certain withdrawal movement and then checking how far it returns forward towards its original position due to the vacuum generated. Should the device be leaking anywhere the piston will not fully attain its original position after being released and the extraction cylinder involved can either be repaired or considered a reject. Once the vacuum-test is successful the plug 20 is pushed sufficiently forward until it snaps into place in the rear end of the extraction cylinder 11. This is best not done until the piston 15 is in the forwardmost position in the extraction cylinder 11. If the ratchet key 17 has already detented behind the rearmost tooth 41''' (FIG. 1) the plug 20 can be moved forward by forwarding the piston rod 14, this necessitating, however, brief venting by slightly backing off the screw caps 25. However, as already mentioned, it is better practice to arrange the plug 20 free to slide between the handle 24 and the toothing 16 because this way the piston 15 can first be brought into the forwardmost position with the screw cap 25 still unscrewed, i.e. then screwing on the screw cap 25 and carrying out the vacuum-test in the manner as already described. The plug 20 is then free to detent in the rear end of the extraction cylinder 11 separately with the piston 15 already in its final position.

The procedure for extracting blood is then as follows:

The guide sleeve 27 is mounted on the boss 26 (FIG. 2) the rear part 12a of the needle 12 piercing the diaphragm 22. The vein can then be punctured and blood extracted by withdrawing the piston 15. In doing so, the ratchet key 17 as shown in FIG. 1 detents from one tooth to the next of the ratchet toothing 16. If the handle 24 is released or should it be attempted to move it in the opposite direction towards the screw cap 25 this is prevented by the ratchet key 17 locking in the tooth 41 present at that time of the ratchet toothing 16. The same applies accordingly to embodiment (FIG. 5) where the wedges 36 prevent a reversal of the movement of the piston rod in the direction of the screw cap 25.

The invention is thus also suitable for creating a vacuum by retracting the piston rod 14 before the guide sleeve 27 is mounted on the boss 26. Whilst in known blood extraction devices of this kind the piston must first be locked into place in the fully retracted position by a companion ratchet of the extraction cylinder 11, the invention provides locking even when the piston 15 is retracted only slightly so that creation of the vacuum can be interrupted in every retracted position of the piston 15, thus making it possible to create even a much weaker vacuum than attainable with the piston 15 fully retracted which can be of advantage e.g. with patients having poor or sensitive veins. In this way the amount of blood extracted in vacuum extraction can also be limited as desired, there being no possibility for the vacuum to collapse due to the one-way coaxial means provided, should the piston be forwarded either intentionally or accidentally.

The invention thus prevents not only intentional or unintentional retraction of the piston 15 but also permits creating and maintaining the desirable vacuum within the extraction cylinder 11 precisely.

To be able to fit the plug 20 particularly easily—to the extent that it surrounds the piston rod 14 as illustrated in the examples of the embodiments—it can be split into two along an axial parting line 21 as shown in FIG. 4 and both parts fitted around the piston rod 14 suitably during assembly.

It is, however, also possible to unscrew the handle 24 (FIGS. 1, 3) or the rear end-piece 14' of the piston rod 14, to then mount the plug 20 from the rear on the untoothed end position of the piston rod 14 before screwing the handle 24 or the end-piece 14' back on.

The piston can also feature an unround cross-section passing through a suitable unround guide opening 13 in the plug 20 to thus ensure perfect angular positioning of the piston rod 14 relative to the plug. 20.

When the piston 15 is fully retracted the screwed-in piston rod 14 as shown in FIG. 1 can be screwed out, requiring however, the piston 15 to be locked in place in the rear end of the extraction cylinder 11 in a manner not illustrated. In addition, the portion 40 ahead of the ratchet toothing 16 must have a cross-section to permit turning of the piston rod 14 relative to the fixed piston 15 when the latter is fully retracted.

It is, however, also possible that the piston 15 is locked in its most retracted position by the forwardmost tooth 41' of the ratchet toothing 16 detenting behind the ratchet key 17 and then by breaking off the piston rod 14 at an intended position 42 behind the first tooth 41'. Tooth 41' can thus, one and the same, be used to prevent return movement of the piston 15 as well as to lock the piston 15 in the fully retracted position.

As indicated by FIG. 6 the toothing 16 provided on the piston rod 14 comprises a row of spring lugs 41'' arranged along the piston rod 14, extending forwards and away from the piston rod 14 in equal spacing. These spring lugs 41'' are formed stiff to compression forces but able to spring-retract radially inwards towards the piston rod 14.

Instead of the ratchet key 17 as shown in FIGS. 1 and 3 an annular shoulder 17' is provided on the plug 20 in the region of the toothing 16 projecting rigidly into the space 13a radially inwards, this shoulder being spaced 43 from the piston rod 14 so that when the piston rod 14 is retracted the spring lugs 41'' are able to pass through the gap stemming from the space 43 by spring-contraction before snapping into place behind the annular shoulder 17' as shown in FIG. 6 for the rearmost spring lug.

A supporting wall 44 extending rearwards and running parallel to the piston rod 14 is in radial outward connection with the end of the annular shoulder 17'. This supporting wall 44 is in contact with the spring lugs 41'' snapped into place behind the annular shoulder 17' radially and inwards. This arrangement prevents, for instance, radial unspringing of the spring lug in place behind the shoulder 17' when the piston rod 14 is forwarded out of the position as shown in FIG. 6.

When the piston 15 or the piston rod 14 is retracted from the position as shown in FIG. 6 the spring lugs 41" snap into place, one after the other, behind the rigid annular shoulder 17' and when the movement is reversed the spring lug 41" which is just behind the annular shoulder 17' mates in the space between the annular shoulder 17' and the supporting wall 44 thus making reversed movement impossible in this example of an embodiment too.

I claim:

1. A method for vacuum testing a blood extraction device having an extraction cylinder featuring a forward end for attaching a needle and a rear end defining an axial guide opening for a piston rod;
   a piston rod having a front end and a handle end;
   a piston;
   said piston rod and said piston being arranged for axial sliding in said extraction cylinder, said piston being detachably secured to the front end of said piston rod;
   one-way coacting means provided to act over substantially the full travel of said piston permitting movement of said piston substantially in one direction from the forward end of said extraction cylinder toward the rear end thereof while substantially preventing movement of the piston in the opposite direction;
   rotational control means for preventing the disengagement of said one-way coacting means;
   said one-way coacting means being located at the rear of said extraction cylinder and defined by a plug for connection to the extraction cylinder at the rear end thereof, said plug defining said guide opening for said piston rod, said plug being adapted to be fixed to the end of said extraction cylinder, so that said plug remains in position when removing or inserting the piston rod from and into said extraction cylinder, respectively;
   the vacuum testing method comprising the steps of locating said plug at the rear end of said extraction cylinder without fixing it to the extraction cylinder;
   vacuum testing the piston;
   thereafter positioning the piston in its forwardmost end position; and
   thereafter moving said plug into its final position on said rear end and thereby fixing it to said extraction cylinder.

2. A method according to claim 1, including the step of fixing the plug to said extraction cylinder by inserting the plug from the rear into the rear end of the cylinder.

3. A method according to claim 1, including the step of surrounding said piston rod with said plug.

4. A method according to claim 3, including splitting said plug axially in first and second parts, and surrounding said piston rod with said plug by placing said parts about the rod.

5. A method according to claim 1, wherein said piston rod includes a removable handle, and placing said plug over said piston rod from a rear end of said piston rod.

6. A method according to claim 1 further comprising the steps of first moving said piston sufficiently forward into the vented forward end of said extraction cylinder so that said plug is just about to attain its final position on the rear end of said extraction cylinder in which it becomes fixed thereto;
   thereafter sealing the forward end of said extraction cylinder;
   thereafter moving said piston toward the rear end of said extraction cylinder and then releasing said piston so that a vacuum formed in the forward end of said extraction cylinder causes movement of said piston towards its original position; and
   monitoring movement of the plug to its original position;
   whereby said plug on completion of successful vacuum testing will be located in the position at which it is fixable attached to the rear end of said extraction cylinder.

7. A method for vacuum testing a blood extraction device having a piston rod;
   an extraction cylinder featuring a forward end for attaching a needle and a rear end defining an axial guide opening for said piston rod;
   said piston rod having a front end and a handle and;
   a piston;
   said piston rod together with said piston being arranged for axial sliding in said extraction cylinder with said piston detachably secured to the front end of said piston rod;
   a rotationally symmetrical, one-way coacting means provided to act over substantially the full travel of said piston rod for permitting movement of said piston substantially in one direction from the forward end of said extraction cylinder to the rear end thereof while substantially preventing movement of the piston in the opposite direction, said one-way coacting means including a plug, and being disposed at the rear end of said extraction cylinder and formed integral with said plug, said plug being adapted for insertion into the rear end of said extraction cylinder;
   said plug also defining the guide opening for said piston rod and being fixably attachable to said extraction cylinder;
   the vacuum testing method comprising the steps of locating said plug at the rear end of said extraction cylinder without fixing it to the extraction cylinder;
   vacuum testing the piston;
   thereafter positioning the piston in its forwardmost end position; and
   thereafter moving said plug into its final position on said rear end and thereby fixing it to said extraction cylinder.

8. A method according to claim 7 further comprising the steps of first moving said piston sufficiently forward into the vented forward end of said extraction cylinder so that said plug is just about to attain its final position on the rear end of said extraction cylinder in which it becomes fixed thereto;
   thereafter sealing the forward end of said extraction cylinder;
   thereafter moving said piston toward the rear end of said extraction cylinder and then releasing said piston so that a vacuum formed in the forward end of said extraction cylinder causes movement of said piston toward its original position; and
   monitoring movement of the plug to its original position;
   whereby said plug on completion of successful vacuum testing will be located in the position at which it is fixed to the rear end of said extraction cylinder.

* * * * *